United States Patent [19]
Chikama

[11] Patent Number: 5,143,475
[45] Date of Patent: Sep. 1, 1992

[54] BENDING DEVICE

[75] Inventor: Toshio Chikama, Tokyo, Japan

[73] Assignee: Kabushiki Kaisha Machida Seisakusho, Tokyo, Japan

[21] Appl. No.: 669,611

[22] Filed: Mar. 14, 1991

[30] Foreign Application Priority Data

Mar. 14, 1990 [JP] Japan ................................. 2-61201

[51] Int. Cl.⁵ ........................... F16B 5/07; A61B 1/00
[52] U.S. Cl. .................................. 403/291; 403/220; 128/4; 248/160
[58] Field of Search ............... 403/291, 220, 223, 41; 128/4; 138/120; 248/104, 160; 604/280; 174/109, 86, 21 CA

[56] References Cited

U.S. PATENT DOCUMENTS

| | | | |
|---|---|---|---|
| 3,060,972 | 10/1962 | Sheldon | 128/772 X |
| 3,162,214 | 12/1964 | Bazinet, Jr. | 128/4 X |
| 3,583,393 | 6/1971 | Takahashi | 138/120 X |
| 3,788,303 | 1/1974 | Hall | 128/4 |
| 3,998,216 | 12/1976 | Hosono | 128/6 |
| 4,351,323 | 9/1982 | Ouchi et al. | 128/4 |
| 4,432,349 | 2/1984 | Oshiro | 138/120 X |
| 4,655,257 | 4/1987 | Iwashita | 128/4 X |
| 4,834,069 | 5/1989 | Umeda | 128/4 |
| 5,069,486 | 12/1991 | Kimura et al. | 138/120 X |

FOREIGN PATENT DOCUMENTS

| | | | |
|---|---|---|---|
| 29344 | 5/1981 | European Pat. Off. | 128/4 |
| 2163653 | 6/1972 | Fed. Rep. of Germany | 128/4 |
| 3534479 | 9/1985 | Fed. Rep. of Germany. | |
| 52-631 | 1/1977 | Japan. | |
| 55-10605 | 1/1980 | Japan. | |
| 58-130025 | 8/1983 | Japan. | |

Primary Examiner—Randolph A. Reese
Assistant Examiner—Harry C. Kim
Attorney, Agent, or Firm—Fish & Richardson

[57] ABSTRACT

There is disclosed a bending device for use in an endoscope or the like. The bending device includes an articulation assembly constituted by a number of segments. In order to increase the rigidity of the articulation assembly in its radial direction, each segment has such a simple configuration that the segment can be formed by bending a hard metal plate such, for example, as a hard spring metal. More specifically, the segment has a semi-cylindrical portion and a pair of extension portions extending respectively from opposite circumferential ends of the semi-cylindrical portion in a direction of the circumference of the semi-cylindrical portion. A pair of notches are formed respectively in opposite axial ends of the segment at the boundary between each of the opposite circumferential ends of the semi-cylindrical portion and each of the extension portions. The notches of the adjacent segments are engaged with each other so that the adjacent segments can be angularly movable relative to each other about those portions of the adjacent segments engaged with each other. The extension portions of each of the segments are disposed inwardly of the semi-cylindrical portion of its adjacent segment.

5 Claims, 2 Drawing Sheets

BENDING DEVICE

BACKGROUND OF THE INVENTION

This invention relates to a bending device for use in an endoscope or the like.

As is well known, an endoscope comprises a hollow body, a flexible insertion portion extending from the front end of the body, a flexible bending portion extending from the distal end of the insertion portion, and a rigid portion formed on the distal end of the bending portion. An inspection window and an illumination window are formed at the rigid portion. A manipulation dial is mounted on the body, and is connected to the bending portion through an operating wire. The manipulation dial is angularly moved to bend the bending portion so that the inspection window, formed at the rigid portion, can be directed to a desired direction. The bending portion comprises an articulation assembly constituted by a series of segments angularly movably connected to one another.

Japanese Patent Publication No. 631/77 discloses an articulation assembly. Each of segments constituting this articulation assembly has a semi-cylindrical portion, and a pair of auxiliary tubular portions of a very small diameter formed respectively on the opposite circumferential ends of the semi-cylindrical portion. A number of segments are disposed along a line in such a manner that the semi-cylindrical portions of any two adjacent segments are directed in opposite directions, respectively, with the auxiliary tubular portions of one of the two adjacent segments aligned respectively with the auxiliary tubular portions of the other segment. A pair of limiting wires are passed respectively through the oppositely-disposed two rows of aligned auxiliary tubular portions to interconnect the segments in such a manner as to prevent the segments from moving radially relative to one another. A guide portion is formed on the circumferentially central section of the semi-cylindrical portion of each segment which is circumferentially spaced 90° from the auxiliary tubular portions, and an operating wire is passed through the guide portions of the segments.

In the articulation assembly of the above construction, since the segment has the auxiliary tubular portions of a very small diameter formed respectively at the opposite circumferential ends thereof, a plate or strip of relatively soft metal must be used when the segment is formed by bending the metal plate. Therefore, when a compressive force is applied to the segment in the radial direction of the segment, the segment is liable to be deformed into a flattened configuration, and various parts received inside the segments are compressed, and in the worst case, such parts may be damaged.

The prior art includes Japanese Laid-Open (kokai) Patent Application No. 130025/83 which shows in FIG. 7 an articulation assembly comprising a number of cylindrical segments. The segment has two pairs of engaging portions. One pair of engaging portions are radially opposed to the other pair of engaging portions. Each pair of engaging portions are spaced from each other in the axial direction of the segment. Each engaging portion has a pair of pieces projecting from the edge of the segment in the axial direction of the segment. One of the pair of pieces slightly projects radially outwardly from the outer peripheral surface of the segment, and the other piece slightly projects radially inwardly from the inner peripheral surface of the segment. The engaging portions of any two adjacent segments are engaged with each other to form the articulation assembly.

Japanese Laid-Open Utility Model Application No. 10605/80 discloses a segment in the form of a flat plate, and this segment has a pair of V-shaped notches, and the notches of any two adjacent segments are engaged with each other.

SUMMARY OF THE INVENTION

It is an object of this invention to provide a bending device comprising an articulation assembly which can withstand a high compressive force acting in a radial direction of the articulation assembly.

According to the present invention, there is provided a bending device comprising:

(a) an articulation assembly comprising a number of segments, each of the segments having a semi-cylindrical portion and a pair of extension portions extending respectively from opposite circumferential ends of the semi-cylindrical portion in a direction of the circumference of the semi-cylindrical portion, a pair of notches being formed respectively in opposite axial ends of the segment at the boundary between each of the opposite circumferential ends of the semi-cylindrical portion and each of the extension portions, a number of the segments being arranged along a line in such a manner that the semi-cylindrical portions of any two adjacent ones of the segments are directed in opposite directions, respectively, the pair of notches in one axial end of one of the adjacent segments being engaged respectively with the pair of notches in one axial end of the other segment opposed to the one axial end of the one segment, so that the adjacent segments can be angularly movable relative to each other about those portions of the adjacent segments engaged with each other, the pair of extension portions of the one segment being disposed inwardly of the semi-cylindrical portion of the other segment, and the pair of extension portions of the other segment being disposed inwardly of the semi-cylindrical portion of the one segment; and (b) operating wire means for bending the articulation assembly, the operating wire means being subjected at its proximal end to an operating force, and the operating wire means being fixed at its distal end to a distal end of the articulation assembly.

DESCRIPTION OF THE PREFERRED EMBODIMENT OF THE INVENTION

A preferred embodiment of the invention will now be described with reference to the drawings.

Figure 1:
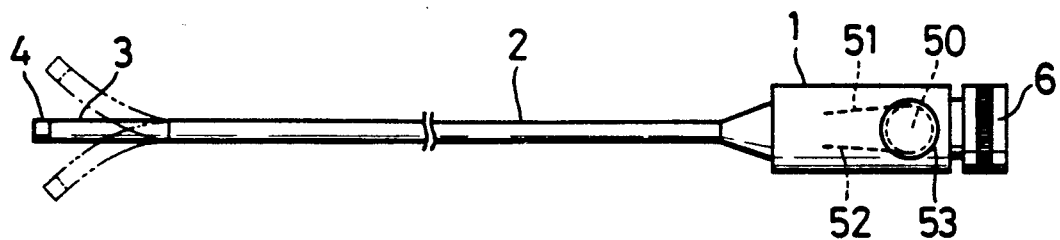
FIG. 1 is a front-elevational view of an endoscope incorporating a bending device according to the present invention.

An endoscope shown in FIG. 1 comprises a hollow body 1, an insertion portion 2 extending from the front end of the body 1, a bending portion (bending device) 3 extending from the distal end of the insertion portion 2, and a rigid portion 4 formed on the distal end of the bending portion 3. The insertion portion 2 and the bending portion 3 are of a tubular shape, and are so flexible as to be bent.

An ocular tube 6 is mounted on the rear end of the body 1. A cable (not shown) is connected at one end to the side wall of the body 1, and a connector (not shown) connectable to a light source is connected to the other end of this cable.

An inspection window and an illumination window are formed at the rigid portion 4. The ocular tube 6 is optically connected to the inspection window via an image-transmitting optical system (not shown) including an optical fiber bundle passing through the body 1, the insertion portion 2 and the bending portion 3. Illumination light from the light source is supplied to the illumination window via an optical fiber bundle passing through the connector, the cable, the body 1, the insertion portion 2 and the bending portion 3.

The insertion portion 2 comprises a spirally-wound strip, a braid fitted on this strip, and a resin tube fitted on the braid. The bending portion 3 comprises an articulation assembly 10 (later described), a braid fitted on the articulation assembly 10, and a resin tube fitted on this braid. The braid and the resin tube of the bending portion 3 are softer than the braid and the resin tube of the insertion portion 2, respectively.

Figure 2:
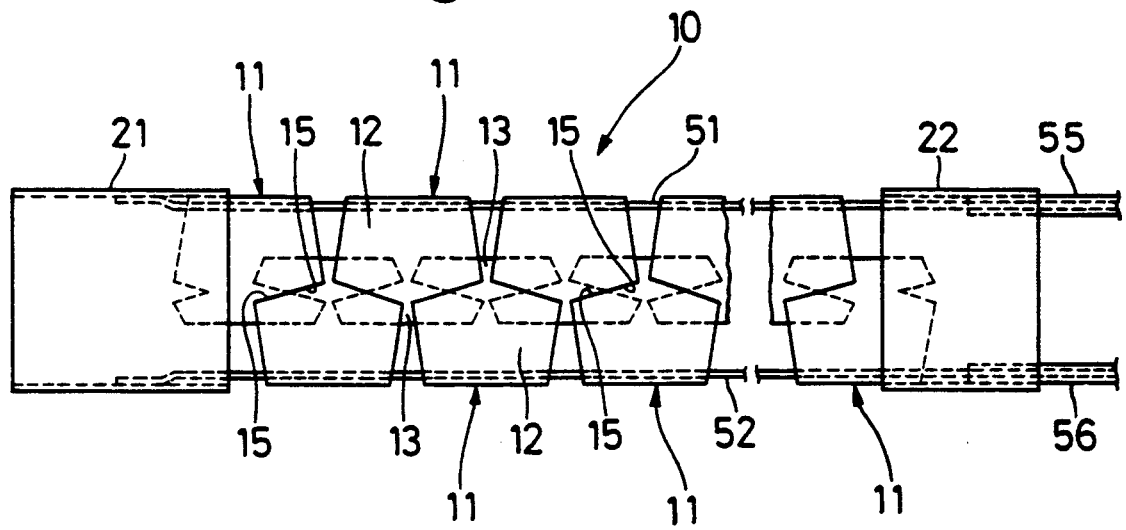
FIG. 2 is a front-elevational view of an articulation assembly of the bending device.

The construction of the bending portion 3 will now be described in detail with reference to FIGS. 2 to 6. As shown in FIG. 2, the bending portion 3 comprises the articulation assembly 10 which has a generally cylindrical shape as a whole. The above-mentioned optical fiber bundles and etc., are passed through the interior (internal space) of the articulation assembly 10. The articulation assembly 10 comprises a number of segments 11 of identical shape.

Figure 5:
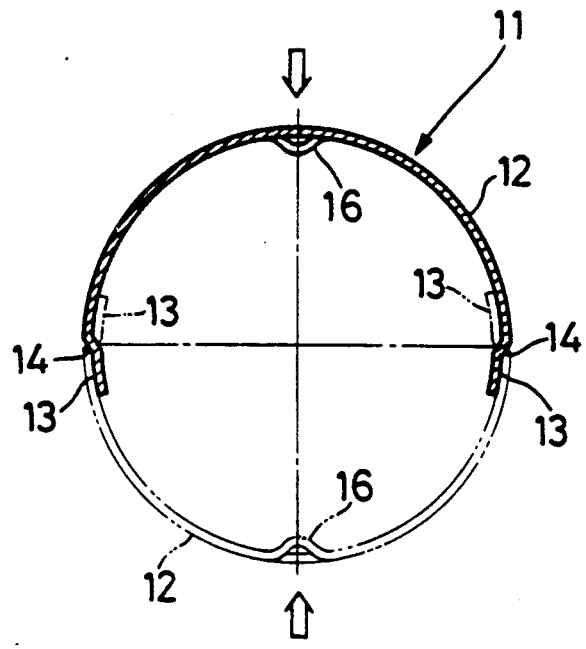
FIG. 5 is a transverse cross-sectional view of the segment.
Figure 6:
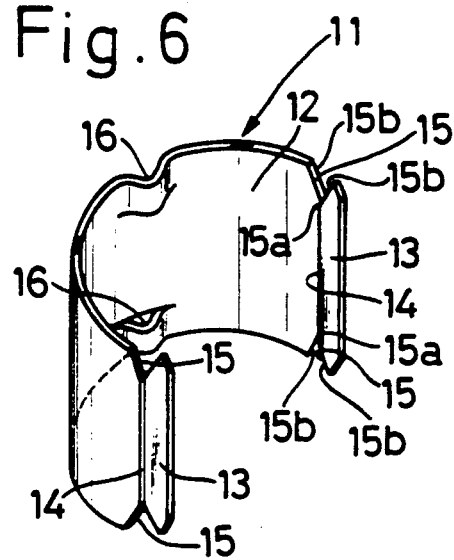
FIG. 6 is a perspective view of the segment.

As best shown in FIGS. 5 and 6, the segment 11 has a semi-cylindrical portion 12 extending over generally 180°, and a pair of extension portion 13 extending respectively from opposite circumferential ends of the semi-cylindrical portion 12. Each extension portion 13 has the shape of an arc disposed on a circle substantially concentric with a circle in which the semi-cylindrical portion 12 lies. The radius of curvature of the outer peripheral surface of the extension portion 13 is substantially equal to the radius of curvature of the inner peripheral surface of the semi-cylindrical portion 12. A step 14 is formed at the boundary between the semi-cylindrical portion 12 and each extension portion 13. The step 14 is inclined, for example, generally 45° with respect to an imaginary line which passes radially transversely of the semi-cylindrical portion 12 and through the center of the circle in which the semi-cylindrical portion 12 lies. The width of the semi-cylindrical portion 12 in its axial direction is narrowed at its circumferentially central section, and increases progressively toward the opposite circumferential ends of the semi-cylindrical portion 12. A pair of V-shaped notches 15 are formed respectively in the opposite axial ends of the segment 11 at the boundary between each of the opposite circumferential ends of the semi-cylindrical portion 12 and each extension portion 13, the pair of V-shaped notches 15 opening away from each other in the direction of the axis of the segment 11. A bottom 15a of the notch 15 is in registry with the step 14. Opposed side edges 15b of the notch 15 are inclined at the same angle with respect to an imaginary line passing through the bottom 15a in the direction of the axis of the segment 11.

A pair of guide portions 16 are formed on the circumferentially central section of the semi-cylindrical portion 12, and are spaced from each other in the direction of the axis of the semi-cylindrical portion 12. The guide portions 16 are circumferentially spaced 90° from the notches 15. The guide portions 16 projects radially inwardly from the semi-cylindrical portion 12.

Figure 3:
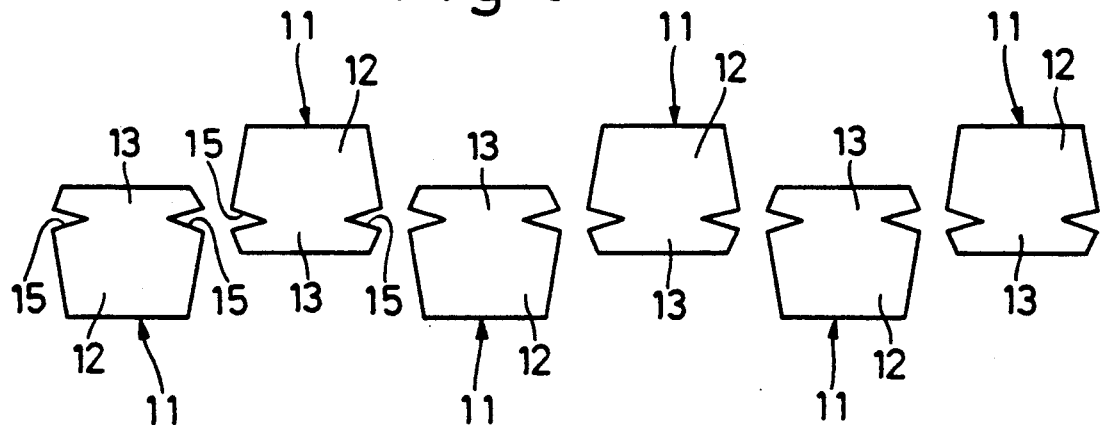
FIG. 3 is an exploded, perspective view of a portion of the articulation assembly.
Figure 4:
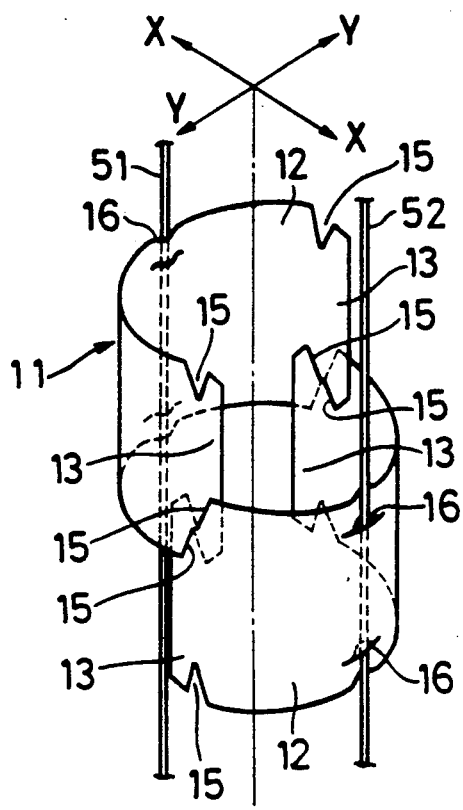
FIG. 4 is a perspective view showing the condition of engagement between adjacent segments of the articulation assembly.

For the sake of simplicity of the illustration, the steps 14 are omitted in FIGS. 2 to 4, and are shown only in FIGS. 5 and 6. Also, the guide portions 16 are omitted in FIGS. 2 and 3, and are shown only in FIGS. 4 to 6.

Figure 7:
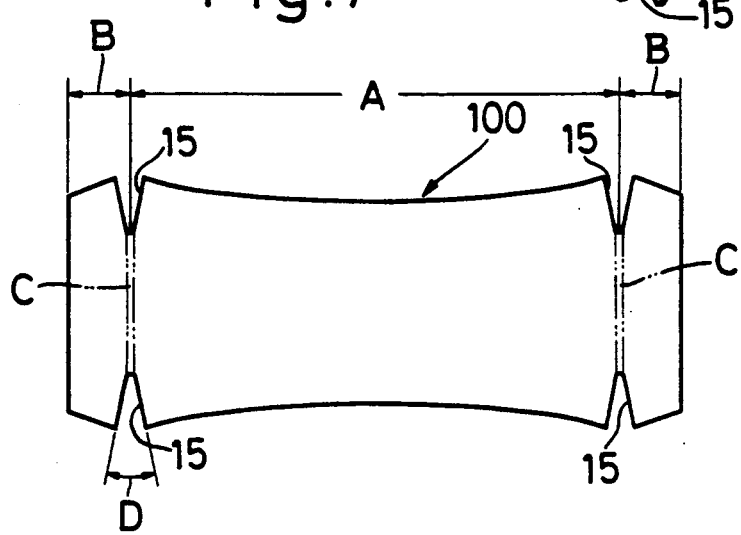
FIG. 7 is a plan view of a metal plate serving as a material for the segment.

The segment 11 of the above construction is formed by bending a metal plate 100 shown in FIG. 7. That portion of the plate 100 indicated by reference character A serves as the semi-cylindrical portion 12, and opposite end portions B of the plate 100 serve as the extension portions 13, respectively. Those portions of the plate 100 indicated by reference character C serve as the steps 14, respectively. The notches 15 are beforehand formed in the plate 100. The segment 11 does not have any tubular portion of a very small diameter, and has such a shape into which the metal plate 100 can be easily bent. Therefore, the metal plate 100 made of a spring material harder than conventionally-used materials can be used as the material for the segment 11.

As shown in FIG. 3, a number of segments 11 of the above construction are arranged along a line in such a manner that the semi-cylindrical portions 12 of any two adjacent segments 11 are directed in opposite directions, respectively, and in this condition the segments 11 are engaged with one another. The condition of engagement between the two adjacent segments 11 will now be described in detail with particular reference to FIG. 4. The pair of notches 15 in one axial end of one segment 11 are engaged or meshed respectively with the pair of notches 15 in one axial end of the other segment 11 opposed to the one axial end of the one segment 11, so that the bottoms 15a of each mating pari of notches 15 are abutted against each other. In this condition, the extension portions 13 of the one segment 11 are disposed inwardly of the semi-cylindrical portion 12 of the other segment 11, and are disposed substantially in contact therewith. Similarly, the extension portions 13 of the other segment 11 are disposed inwardly of the semi-cylindrical portion 12 of the one segment, and are disposed substantially in contact therewith.

The adjacent segments 11 are angularly movable in an X-axis direction about a line which passes through the pair of meshing points (i.e., the bottoms 15a of the intermeshed notches 15) in a Y-axis direction perpendicular to the X-axis direction. The X-axis in FIG. 4 extends in the upward-and-downward direction in FIGS. 1 and 2. Therefore, the articulation assembly 10 can be bent in upward and downward directions in FIGS. 1 and 2.

As shown in FIG. 2, the foremost segment 11 of the articulation assembly 10 is fitted in and fixed to a cylinder 21, and similarly the rearmost segment 11 is fitted in and fixed to a cylinder 22. The front cylinder 21 serves as a frame for the rigid portion 4 of the endoscope. The front end portions of the strip and braid of the insertion portion 2 are fixedly secured to the outer periphery of the rear cylinder 22.

Next, a mechanism for bending the bending portion 3 will now be described. As shown in FIG. 1, this mechanism comprises two operating wires 51 and 52. The operating wires 51 and 52 are fixedly secured at their one ends to an outer peripheral surface of a pulley 50 mounted within the body 1, and extend forwardly from the upper and lower sides of the periphery of the pulley 50, respectively. The pulley 50 is connected to a manipulation dial 53, mounted outside of the body 1, via a shaft (not shown) extending through the side wall of the body 1.

As shown in FIG. 2, at the insertion portion 2, the operating wires 51 and 52 are passed respectively through flexible guide tubes 55 and 56 of a small diameter. Each of the guide tubes 55 and 56 is formed by spirally winding a wire. The rear ends of the guide tubes 55 and 56 are fixedly secured to the body 1 in radially opposed relation to each other, that is, in opposed relation to each other in the upward-and-downward direction in FIG. 1. The front ends of the guide tubes 55 and 56 are fixedly secured to the inner peripheral surface of the cylinder 22 in opposed relation to each other in the upward-and-downward direction.

As shown in FIGS. 2 and 4, at the bending portion 3, one operating wire 51 is passed through the guide portions 16 of alternate segments 11, and the other operating wire 52 is passed through the guide portions 16 of the other alternate segments 11. The front ends of the operating wires 51 and 52 are fixedly secured to the inner peripheral surface of the cylinder 21 in radially opposed relation to each other, that is, in opposed relation to each other in the upward-and-downward direction in FIG. 2.

In the endoscope of the above construction, when the manipulation dial 53 is angularly moved in a counter-clockwise direction (FIG. 1), the operating wire 52 is pulled whereas the operating wire 51 is loosened, so that the bending portion 3 is bend downward in FIG. 1. In contrast, when the manipulation dial 53 is angularly moved in a clockwise direction, the bending portion 3 is bent upward.

The maximum angle of angular movement of the adjacent segments 11 relative to each other is determined by the angle D (see FIG. 7) of opening of the notch 15 defined by its opposed side edges 15b and 15b, because the side edges 15b of the notches 15 of one of the adjacent segments 11 are brought into engagement with the steps 14 of the other segment 11, respectively. The maximum angle of angular movement of the adjacent segments 11 relative to each other may be determined by the engagement of the edges of the semi-cylindrical portions 12 of the adjacent segments 11 with each other.

The articulation assembly 10 of the above construction can withstand a much higher radial compressive force than the conventional articulation assemblies can, and is less liable to be deformed or flattened, thereby protecting the optical fiber bundles and etc., received within this assembly.

One reason for this is that the segment 11 can be formed by bending the plate 100 of hard spring metal since any portion of the segment 11 does not need to be worked or formed into a small radius of curvature, as described above. The segment 11 can well withstand the compressive force particularly acting in the Y-axis direction (FIG. 4).

Another reason is that the extension portions 13 of one of the adjacent segments 11 are disposed in contact with the inner peripheral surface of the semi-cylindrical portion 12 of the other segment 11 at the opposite end portions of this semi-cylindrical portion 12, and that similarly, the extension portions 13 of the other segment 11 are disposed in contact with the inner peripheral surface of the semi-cylindrical portion 12 of the one segment 11 at the opposite end portions of this semi-cylindrical portion 12. When a compressive force acts on the segment 11 in the X-axis direction (FIG. 4), that is, in a direction of an arrow in FIG. 5, the segment 11 tends to be flattened. At this time, the extension portions 13 of the one segment 11 tend to be angularly moved outwardly about the meshing points of the intermeshed notches 15 of the adjacent segments 11 whereas the opposite end portions of the semi-cylindrical portions 12 of the other segment 11 tend to be angularly moved inwardly about these meshing points. As a result, the extension portions 13 are firmly abutted against the opposite end portions of the semi-cylindrical portions 12, thereby mutually limiting their movements. Similarly, the extension portions 13 of the other segment 11 and the opposite end portions of the semi-cylindrical portion 12 of the one segment 11 mutually limit their movements. Thus, the adjacent segments 11 cooperate with each other to prevent their deformation due to the compressive force.

The present invention is not limited to the above embodiment, and various modifications can be made. For example, in the case where the segment is formed by a very hard, thin plate, the semi-cylindrical portion and the extension portions may have the same radius of curvature, with the steps omitted. The extension portion may be generally flat since it is short in the circumferential direction. Further, when the bending portion is required to be bent in only one direction, only one operating wire is used.

The bending device of the present invention can be applied to an electronic endoscope utilizing an image sensor and a surgical catheter.

What is claimed is:

1. A bending device comprising:
(a) an articulation assembly comprising a number of segments, each of said segments having a semi-cylindrical portin and a pair of extension portions extending respectively from opposite circumferential ends of said semi-cylindrical portion in a direction of the circumference of said semi-cylindrical portion, a pair of notches being formed respectively in opposite axial ends of said segment at the boundary between each of the opposite circumferential ends of said semi-cylindrical portion and each of said extension portions, a number of said segments being arranged along a line in such a manner that said semi-cylindrical portions of any two adjacent ones of said segments are directed in opposite directions, respectively, said pair of notches in one axial end of one of the adjacent segments being engaged respectively with said pair of notches in one axial end of the other segment opposed to the one axial end of said one segment, so that the adjacent segments can be angularly movable relative to each other about those portions of said adjacent segments engaged with each other, said pair of extension portions of said one segment being disposed inwardly of said semi-cylindrical portion of said other segment, and said pair of extension portions of said other segment being disposed inwardly of said semi-cylindrical portion of said one segment; and (b) operating wire means for bending said articulation assembly, said operating wire means being subjected at its proximal end to an operating force, and said operating wire means being fixed at its distal end to a distal end of said articulation assembly.

2. A bending device according to claim 1, in which said pair of extension portions of each of said segments are disposed in contact with the inner peripheral surface of said semi-cylindrical portion of said segment disposed adjacent thereto.

3. A bending device according to claim 2, in which each of said pair of extension portions has the shape of an arc disposed on a circle subtantially concentric with a circle in which said semi-cylindrical portion lies.

4. A bending device according to claim 3, in which the radius of curvature of the outer peripheral surface of said extension portion is substantially equal to the radius of curvature of the inner peripheral surface of said semi-cylindrical portion, a step being formed at the boundary between said semi-cylindrical portion and each of said pair of extension portions, and said step extending in the direction of the axis of said segment and being inclined with respect to an imaginary line which passes radially tranversely of said semi-cylindrical portion and through the center of a circle in which said semi-cylindrical portion lies.

5. A bending device according to claim 1, in which each of said notches has a V-shape.

* * * * *

UNITED STATES PATENT AND TRADEMARK OFFICE
CERTIFICATE OF CORRECTION

PATENT NO. : 5,143,475
DATED : September 1, 1992
INVENTOR(S) : Toshio Chikama

It is certified that error appears in the above-indentified patent and that said Letters Patent is hereby corrected as shown below:

Column 6, line 44, "portin" should be --portion--.

Signed and Sealed this

Nineteenth Day of October, 1993

Attest:

BRUCE LEHMAN

Attesting Officer

Commissioner of Patents and Trademarks